(12) United States Patent
Bagwell

(10) Patent No.: US 7,739,902 B2
(45) Date of Patent: Jun. 22, 2010

(54) PORTABLE SOLUTION DETECTOR FOR IDENTIFYING CHEMICAL SOLUTIONS INCLUDING FROM CHEMICAL SPILLS

(75) Inventor: Cathy Ann Bagwell, Rowlett, TX (US)

(73) Assignee: Texas Instruments Incorporated, Dallas, TX (US)

( * ) Notice: Subject to any disclaimer, the term of this patent is extended or adjusted under 35 U.S.C. 154(b) by 329 days.

(21) Appl. No.: 12/039,484

(22) Filed: Feb. 28, 2008

(65) Prior Publication Data

US 2009/0217756 A1 Sep. 3, 2009

(51) Int. Cl.
*G01N 29/00* (2006.01)
(52) U.S. Cl. .................. 73/61.51; 73/53.01
(58) Field of Classification Search ........... 73/53.01, 73/54.06, 54.12, 61.44, 61.51
See application file for complete search history.

(56) References Cited

U.S. PATENT DOCUMENTS

| | | | | |
|---|---|---|---|---|
| 3,222,918 A | * | 12/1965 | Kuntz et al. | 73/53.01 |
| 3,874,223 A | * | 4/1975 | Miyazaki et al. | 73/32 R |
| 4,811,592 A | * | 3/1989 | Miura et al. | 73/32 A |
| 5,444,383 A | * | 8/1995 | Agar et al. | 324/697 |
| 5,743,135 A | * | 4/1998 | Sayka et al. | 73/293 |

* cited by examiner

*Primary Examiner*—Hezron Williams
*Assistant Examiner*—Rodney T Frank
(74) *Attorney, Agent, or Firm*—Wade J. Brady, III; Frederick J. Telecky, Jr.

(57) ABSTRACT

A detector and detection method for identifying unknown chemical solutions following chemical spills includes a specific gravity detector including a detector column having an inlet end operable to collect a sample of a solution, wherein the detector column is formed of an optically transparent material to allow visual observation of the sample in the detector column. At least a first plurality of specific gravity floats including a first specific gravity float is located and moveable within the detector column, wherein the first specific gravity float has a density to float in liquids having a specific gravity of greater than a first density level. At least a second specific gravity float is located and moveable within the detector column, wherein the second specific gravity float has a density to float in liquids having a specific gravity greater than the first density level. A sample of an unknown solution from a site of a chemical spill is introduced into the detector column. A float response of the first plurality of specific gravity floats is observed and based on the observation a presence or absence of at least one chemical solution in the unknown solution is identified.

19 Claims, 3 Drawing Sheets

PORTABLE SOLUTION DETECTOR FOR IDENTIFYING CHEMICAL SOLUTIONS INCLUDING FROM CHEMICAL SPILLS

FIELD OF THE INVENTION

The present invention is related to specific gravity solution detectors and related methods for identifying unknown solutions.

BACKGROUND

Although chemical spills are somewhat common in semiconductor manufacturing, they are, for the most part, identifiable and safe to mitigate with proper personal protective equipment [PPE]. It is those times, when the chemical is non-detectable, that can be hazardous. The hazards resulting from a spill depend on variables that include the spilled material's chemical and physical properties, location, and quantity.

Some chemicals are difficult to detect even from a list of commonly available detectors, particularly those which are colorless, have low vapor pressure, and have a near neutral pH. Hydrogen fluoride (HF) readily dissolves in water to form colorless, extremely corrosive hydrofluoric acid solutions. HF solutions are visibly indistinguishable from water. However, HF solutions can be detected with a variety of detectors. In semiconductor manufacturing, HF solutions are commonly used for oxide etching, including solutions such as so called buffered HF (BHF). BHF is a neutral solution and generally comprises 40-45% Ammonium Fluoride; 0.49% Hydrofluoric Acid, with the remaining balance being water. BHF is thus an example of a chemical solution that is non-detectable outside a laboratory setting, even from a list of commonly available field detectors, since BHF is colorless, has a low vapor pressure, and has a neutral pH.

HF solutions are extremely hazardous. Such solutions can cause severe injury to any tissue with which it comes in contact (chemical burn). Exposure by contact with skin, or by inhalation or ingestion, can lead to severe toxic systemic effects (Acute Fluoride Intoxication) and potentially death. Death can occur from severe electrolytic imbalance (hypocalcemia and hypomagnesaemia) that leads to cardiac arrhythmia (fibrillation), which, in turn, can lead to cardiorespiratory arrest and multiple organ failure (kidney and liver).

HF is also easily absorbed by tissue, penetrating and then rapidly dissociating into Hydrogen and Fluoride. HF is highly corrosive and will destroy tissue, but the fluoride ion will also migrate through, and continue to damage bone. The disassociated fluoride ion will continue reacting to create fluorinated salts, which can cause serious toxic systemic effects. Washing the exposed tissue with water does not neutralize or stop the reaction, which limits the benefits of water washing (decontamination). HF-specific first aid treatments bind the fluoride to calcium, and rapidly starting such treatments is critical to stopping further tissue and bone damage. What is needed is a low cost, portable detector adapted for identifying the presence of certain target chemical solutions from unknown solutions, such as BHF solutions.

SUMMARY

This Summary is provided to comply with 37 C.F.R. §1.73, requiring a summary of the invention briefly indicating the nature and substance of the invention. It is submitted with the understanding that it will not be used to interpret or limit the scope or meaning of the claims.

One embodiment of the invention comprises methods for identifying unknown chemical solutions following chemical spills. The method generally comprises providing a specific gravity detector comprising a detector column having an inlet end operable to collect a sample from an unknown solution from a chemical spill. The detector column is formed of an optically transparent material to allow visual observation of the sample in the detector column. At least a first plurality of specific gravity floats comprise a first specific gravity float located and moveable within the detector column, the first specific gravity float has a density to float in liquids having a specific gravity of greater than a first density level. At least a second specific gravity float is also located and moveable within the detector column, the second specific gravity float having a density to float in liquids having a specific gravity greater than the first density level.

After the sample of unknown solution from the chemical spill into the detector, the specific gravity floats either float or sink depending on the specific gravity of the solution being tested. A float response of the specific gravity floats is observed and a presence or absence of at least one chemical solution in the unknown solution is identified based on results of the observing step. In one embodiment, the unknown solution is gathered within a semiconductor manufacturing facility and has a pH from 6.8 to 7.2. The unknown solution can comprise hydrofluoric acid, such an HF concentration from 0.4% to 2%. In one embodiment, the HF solution is BHF. The method can further comprise the step of chemical strip testing the sample and using results from the chemical strip testing for the identifying step.

In one embodiment a second plurality of specific gravity floats operable to move in a path independent from a path of the first plurality of specific gravity floats is provided, wherein the second plurality of specific gravity floats span a density range outside a density range spanned by the first plurality of specific gravity floats. In this embodiment, the detector can include a plurality of said detector columns, wherein the first plurality of specific gravity floats are in a first detector column and the second plurality of specific gravity floats are in a second detector column.

A gravimetric detector for identifying unknown chemical solutions comprises at least a first and a second detector column each having an inlet end operable to collect a solution, wherein the detector columns are formed of an optically transparent material to allow visual observation of the sample in the detector columns. At least a first plurality of specific gravity floats are located and moveable within the first detector column, wherein the first plurality of specific gravity floats have a density range to sense liquids having a specific gravity in a first specific gravity range. At least a second plurality of specific gravity floats are located and moveable within the second detector column, wherein the second plurality of specific gravity floats having a density range to sense liquids having a specific gravity in a second specific gravity range.

A gravimetric detector for identifying a 0.5 to 2% buffered hydrogen fluoride (BHF) solution comprises a detector column having an inlet end operable to collect a sample of the BHF solution, wherein the detector column is formed of an optically transparent material to allow visual observation of the sample while in the detector column. A plurality of specific gravity floats are located and moveable within the detector column, wherein at least one of the plurality of specific gravity floats up at least a portion of the height of the detector column in the presence of the BHF solution and at least one of the plurality of specific gravity floats does not float up in the detector column in the presence of the BHF solution.

DETAILED DESCRIPTION

Figure 1:
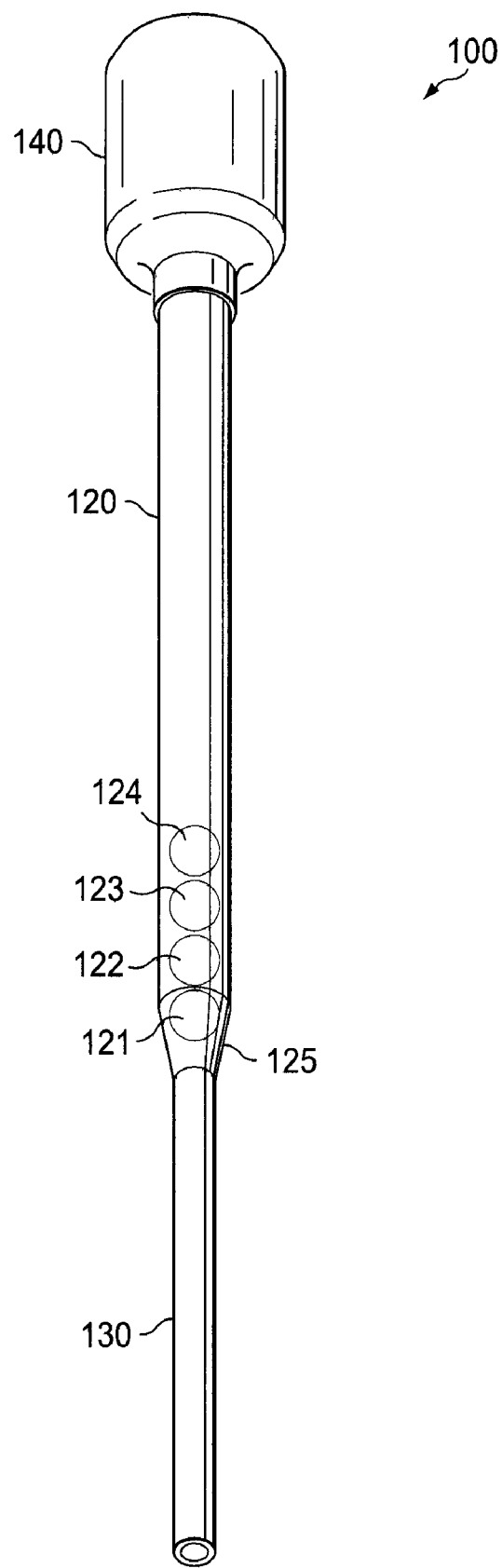
FIG. 1 shows a depiction of a specific gravity detector for identifying unknown chemical solutions, according to an embodiment of the invention.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the invention comprise methods for identifying unknown chemical solutions following chemical spills. The method generally comprises providing a specific gravity detector comprising a detector column having an inlet end operable to collect a solution. The detector column is formed of an optically transparent material to allow visual observation of the sample in the detector column. At least a first plurality of specific gravity floats comprise a first specific gravity float located and moveable within the detector column, the first specific gravity float having a density to float in liquids having a specific gravity of greater than a first density level. At least a second specific gravity float is also located and moveable within the detector column, the second specific gravity float having a density to float in liquids having a specific gravity greater than the first density level. A sample of an unknown solution is introduced from a site of a chemical spill into the detector. The specific gravity floats either float or sink depending on the specific gravity of the solution being tested. A float response of the specific gravity floats is observed and a presence or absence of at least one chemical solution in the unknown solution is identified based on results of the observing step.

In one embodiment of the invention the first specific gravity float and the second specific gravity float have different colors. In a particular embodiment, there are four specific gravity float balls which all have different specific gravities and different colors, such as red, blue, green, and orange.

In one application for the invention the unknown solution is gathered within a semiconductor manufacturing facility, such as within or adjoining a clean room. As known in the art, a variety of solutions are use in semiconductor manufacturing. Some of these solutions have a near neutral pH being from 6.8 to 7.2. As known in the art, solutions having a near neutral pH (e.g. ethylene glycol) generally cannot be distinguished from water based on pH.

The specific gravity floats can be made to service specific needs with a specific gravity range that matches the specific gravity of one or more target chemical solutions. In the case of 1% BHF, the room temperature specific gravity range can be from 1.111 to 1.114.

The introducing step can comprise drawing the sample into the detector column using a transfer pipette-squeeze bulb positioned on an end of the detector column opposite the inlet end. The method can further comprise the step of chemical strip testing the sample, and using results of the chemical strip testing for the identifying step. The chemical strip testing can be used in conjunction with specific gravity testing to identify the presence of oxidizers (e.g. $H_2O_2$), halogens such as iodine and bromine, or organic solvents such as derived from petroleum products.

FIG. 1 shows a depiction of a specific gravity detector 100 for identifying an unknown chemical, according to an embodiment of the invention suitable for identifying unknown chemical solutions following a chemical spill. The gravimetric detector 100 comprises a detector column 120, such as a pipette, having a narrowed (tapered) inlet end 125 operable to collect a solution. A flexible extension member 130 is shown fit over the inlet end to permit solution collection in difficult to reach locations. The detector column 120 is formed of an optically transparent material, such as silica, to allow visual observation of the sample in the detector column 120. A plurality of specific gravity floats comprising floats 121-124 having different specific gravities and different colors are located and sized to be held within the detector column by the narrowed inlet end 125 and be moveable upward within the detector column 120. A transfer pipette-squeeze bulb 140 is shown positioned on an end of the detector column 120 opposite the inlet end 125 for drawing the sample of the unknown solution into the detector column 120.

Air in the tester should be minimized for most accurate testing. If air enters the tester upon drawing the sample, the tester can be tapped, such as with one's finger, to release air bubbles that may have attached to the specific gravity ball.

Specific gravity floats comprising floats can be obtained from Chaslyn Co., 1912 East Meadowmere Ave., Springfield, Miss., 65804, USA. "Chaslyn balls" are made of a wax-like composition called "Chaslynite". Common specific gravity balls range from 1.000 to 1.450 with a degree of accuracy of ±0.002 can be obtained from this vendor. Specialized specific gravity balls can be made to particular specifications upon request. However, embodiments of the invention are not limited to Chaslyn balls.

In one embodiment, gravimetric detector 100 is configured for determining the presence or absence of a BHF solution, such as 100:1 BHF. In this particular embodiment the specific gravity range spanned by the plurality of specific gravity floats is configured to include the room temperature specific gravity of the 100:1 BHF solution. If the unknown solution in the detector column causes a predetermined observed response for the specific gravity floats, generally comprising at least one, but not all, specific gravity float rising in the detector column in the presence of unknown solution, a particular solution such as 100:1 BHF can be identified.

In embodiments of the invention the detector further comprises a second plurality of specific gravity floats operable to move in a path independent from a path of the first plurality of specific gravity floats, the second plurality of specific gravity floats spanning a density range outside a density range spanned by the first plurality of specific gravity floats. One or more added density ranges allows for the identification of a plurality of chemical solutions, generally from a list of known candidate solutions that are known to be present in a given laboratory or manufacturing facility. In the case of semiconductor manufacturing, the second plurality of specific gravity floats can be used to identify 99% ethylene glycol, specific gravity 1.115; 31.5% hydrogen peroxide, specific gravity 1.12; common oxide etch, specific gravity 1.12; and taper etch, specific gravity 1.16.

Figure 2:
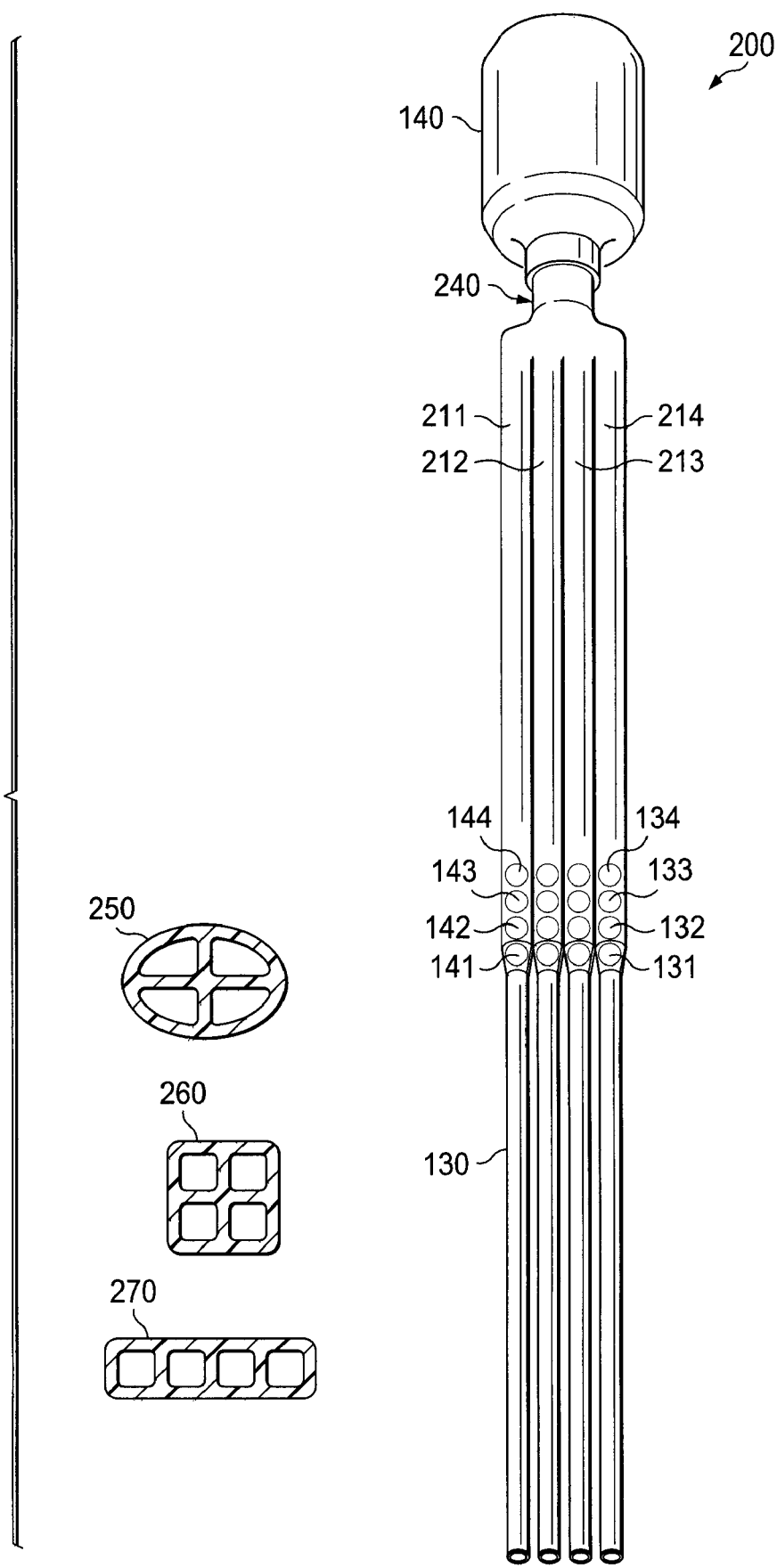
FIG. 2 shows a depiction of a multi-solution specific gravity solution detector according to another embodiment of the invention.

FIG. 2 shows a depiction of a multi-solution gravimetric solution detector 200 according to another embodiment of the invention. Detector 200 is suitable for identifying a plurality of unknown chemical solutions following chemical spills. Detector 200 comprises detector columns 211-214, such as pipettes, each having narrowed inlet ends analogous to narrow end 125 shown in FIG. 1 operable to collect a solution. A flexible extension member 130 is shown fit over the inlet ends to permit solution collection in difficult to reach locations. The detector columns share a common end opposite their inlet ends referred to herein as common region 240. A transfer pipette-squeeze bulb 140 is shown positioned on common region 240 for simultaneously drawing sample into the respective detector columns 211-214.

Each detector column 211-214 includes a plurality of specific gravity floats comprising floats. For example, detector column 211 includes floats 141-144, while detector column 214 includes floats 131-134. The respective plurality of specific gravity floats in each detector column 211-214 are operable to move in a path independent from the path of the other pluralities of specific gravity floats in the other detector columns. The respective plurality of specific gravity floats span different density ranges thus allowing detector 200 to be used for identifying a plurality of unknown chemical solutions, such as following a chemical spill.

A variety of cross sectional configurations are possible the respective detector columns for detector 200. FIG. 2 shows and elliptical/circular cross section 250, a square cross section 260 and a rectangular cross section 270.

Figure 3:
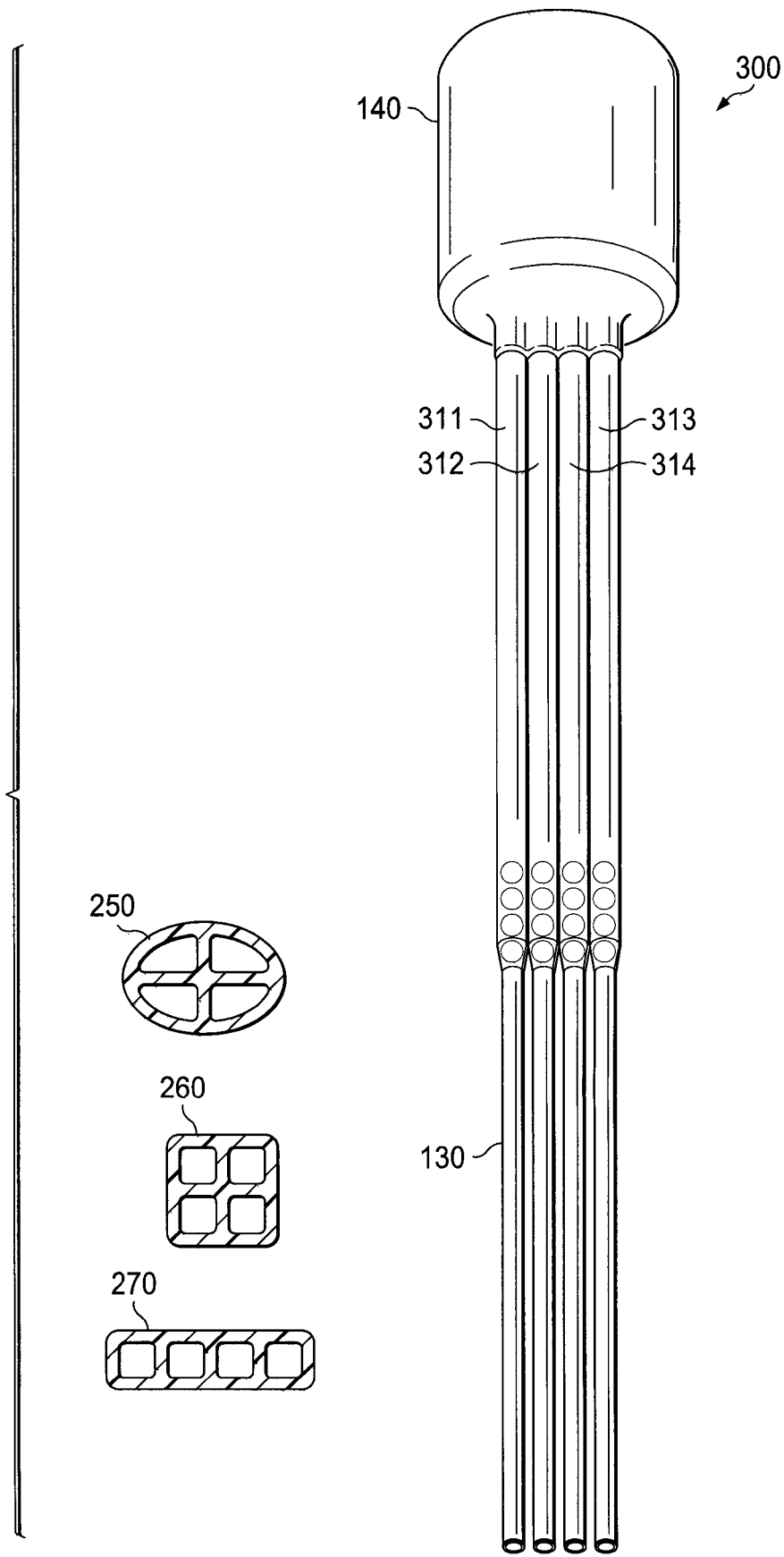
FIG. 3 shows a depiction of a multi-solution specific gravity solution detector according to yet another embodiment of the invention.

FIG. 3 shows a depiction of a multi-solution gravimetric solution detector 300 according to yet another embodiment of the invention. Detector 300 is suitable for identifying a plurality of unknown chemical solutions following chemical spills. Detector 200 comprises detector columns 311-314, such as pipettes, each having narrowed inlet ends analogous to narrow end 125 shown in FIG. 1 operable to collect a solution. A flexible extension member 130 is shown fit over the inlet ends to permit solution collection in difficult to reach locations. Unlike detector 200, the detector columns 311 to 314 do not share a common end opposite their inlet ends.

The positive identification of hazardous chemicals is important to personnel safety. Using detectors according to the invention, the presence of chemicals such as BHF can be determined and appropriate actions can then be taken to remove and stop the contamination from spreading. Also, being able to positively identify the chemical allows selection of appropriate personnel protection equipment.

Detectors according to embodiments of the invention can be used by a wide variety of users and industries. For example, fire departments, HazMat teams, chemical manufacturers, decontamination companies, environmental companies, chemical suppliers, laboratories, university chemical labs and semiconductor manufacturing floors can all benefit from embodiments of the invention.

EXAMPLES

Customized specific gravity detectors/testers were fabricated comprising transfer pipettes having specific gravity "Chaslyn Balls" disposed therein, similar to detector 100 shown in FIG. 1. The Chaslyn Balls were made of a wax-like composition which is highly homogeneous, without air inclusions and is unaffected by the action of sulfuric and most other acids. The Chaslyn Balls comprised a red ball having a density of 1.165, a blue ball having a density of 1.140, green ball having a density of 1.120 and an orange ball having a density of 1.100. The tolerance was ±0.002. The values for the balls was selected based on the specific gravity of the following chemicals to be tested: Water having a specific gravity of 1, a 1% BHF solution ranging from 1.111-1.114, a 31.5% hydrogen peroxide solution equaling 1.12 and a 99% ethylene glycol solution having a specific gravity of 1.115. The solutions were tested at room temperature.

It was discovered that caution should be used so that the test sample did not get aerated. If the operator pulled a sample into the tube and pushed it back into the sample container air was introduced into the sample which was found to cause an inaccurate test result since aerating the solution causes air to gather around the Chaslyn balls, thus distorting the specific gravity results.

HF solution samples of 49%, 5% and 2.5% as well as water, 31.5% hydrogen peroxide and 99% ethylene glycol solution were collected from a simulated spill. For the 1% BHF solution only the Orange Chaslyn ball floated to the surface, all others sunk to the bottom of the tester. As noted above, the Orange Chaslyn ball specific gravity was equal to 1.100. Thus, although the 1% BHF solution does not indicate an acidic or basic pH, nor can it be detected with a chemical classifier strip, it was identified by specific gravity testing according to the invention.

Testing of the 31.5% Hydrogen Peroxide solution revealed the Orange Chaslyn ball floated to the surface, the Green Chaslyn ball floated towards the middle of the tester, and the Blue and Red Chaslyn balls sunk to the bottom of tester. On the basis of the response of the Chaslyn balls alone, the 1% BHF solution was distinguishable from the 31.5% Hydrogen Peroxide solution. The hydrogen peroxide solution can also be detected as an oxidizer by a chemical classifier strip. Thus, a 2 step test can be conducted to identify oxidizers such as Hydrogen Peroxide solutions.

Testing of the 99% Ethylene Glycol solution revealed the Orange Chaslyn ball floated to the surface, the Green Chaslyn ball floated between the middle and the surface, but higher than it did in the 31.5% hydrogen peroxide. The Red and Blue Chaslyn balls sunk to the bottom of the tester. Thus, although ethylene glycol indicates a very weak acid pH and was found to be undetectable using a chemical classifier strip, it was identified by specific gravity testing according to the invention.

Testing of city water and DI water revealed all Chaslyn balls sunk to the bottom of the tester. Given their specific gravity of 1, this response was expected.

Testing of the 5% HF solution revealed all the Chaslyn balls sunk to the bottom of the tester. This is due to the specific gravity of 5% HF being 1.01. The glass pipette tube was observed to begin to etch almost instantly.

Testing of the 49% HF solution revealed the Orange, Blue and Green Chaslyn balls floated higher than the red ball, which was suspended midway. This is due to the specific gravity of the red ball equaling 1.165 being almost equal to the specific gravity of 49% HF which is 1.15-1.18.7. The glass pipette tube was observed to begin to etch almost instantly.

In conclusion, the results of the tests described above evidenced the ability to clearly distinguish between a 1% BHF solution, water, 31.5% hydrogen peroxide and 99% ethylene glycol using specific gravity testers according to embodiments of the invention. The tests were repeated several times with the same results.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In particular regard to the various functions performed by the above described components (assemblies, devices, circuits, systems, etc.), the terms (including a reference to a "means") used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the invention. In addition, while a particular feature of the invention may have been disclosed with respect to only one of several implementations, such feature may be combined with one or more other features of the other implementations as may be desired and advantageous for any given or particular application. Furthermore, to the extent that the terms "including", "includes", "having", "has", "with", or variants thereof are used in either the detailed description and/or the claims, such terms are intended to be inclusive in a manner similar to the term "comprising."

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the following claims.

The invention claimed is:

1. A method for identifying unknown chemical solutions following chemical spills, comprising:
    providing a specific gravity detector comprising a detector column having an inlet end operable to collect a sample of an unknown solution, said detector column formed of an optically transparent material to allow visual observation of said sample in said detector column, at least a first plurality of specific gravity floats comprising a first specific gravity float located and moveable within said detector column, said first specific gravity float having a density to float in liquids having a specific gravity of greater than a first density level, and at least a second specific gravity float located and moveable within said detector column, said second specific gravity float having a density to float in liquids having a specific gravity greater than said first density level;
    introducing a sample of an unknown solution from a site of a chemical spill into said detector column;
    observing a float response of said first plurality of specific gravity floats, and identifying a presence or absence of at least one chemical solution in said unknown solution based on results of said observing.

2. The method of claim 1, wherein said first specific gravity float and said second specific gravity float have different colors.

3. The method of claim 1, wherein said unknown solution is gathered within a semiconductor manufacturing facility.

4. The method of claim 1, wherein said unknown solution has a pH from 6.8 to 7.2.

5. The method of claim 1, wherein said unknown solution comprises hydrofluoric acid.

6. The method of claim 5, wherein said hydrofluoric acid solution has an HF concentration from 0.4% to 2%.

7. The method of claim 6, wherein said hydrofluoric acid solution comprises buffered HF.

8. The method of claim 7, wherein said plurality of specific gravity floats are in a specific gravity range from 1.100 to 1.165.

9. The method of claim 6, wherein said introducing step comprises drawing said sample using a transfer pipette-squeeze bulb positioned on an end of said detector column opposite said inlet end.

10. The method of claim 1, further comprising the step of chemical strip testing said sample and using results from said chemical strip testing for said identifying step.

11. The method of claim 1, further comprising a second plurality of specific gravity floats operable to move in a path independent from a path of said first plurality of specific gravity floats, said second plurality of specific gravity floats spanning a density range outside a density range spanned by said first plurality of specific gravity floats.

12. The method of claim 11, wherein said detector includes a plurality of said detector columns, wherein said first plurality of specific gravity floats are in a first detector column and said second plurality of specific gravity floats are in a second detector column.

13. A gravimetric detector for identifying unknown chemical solutions, comprising:
    at least a first and a second detector column each having an inlet end operable to collect a sample of an unknown chemical solution, said detector columns formed of an optically transparent material to allow visual observation of said sample in said detector columns;
    at least a first plurality of specific gravity floats located and moveable within said first detector column, said first plurality of specific gravity float having a density range to sense liquids having a specific gravity in a first specific gravity range; and
    at least a second plurality of specific gravity floats located and moveable within said second detector column, said second plurality of specific gravity floats having a density range to sense liquids having a specific gravity in a second specific gravity range.

14. The detector of claim 13, wherein said first and second detector columns sharing a common end opposite said inlet end.

15. The detector of claim 14, further comprising a transfer pipette-squeeze bulb positioned on said common end.

16. The detector of claim 13, wherein said first or second plurality of specific gravity floats sense a specific gravity range from 1.100 to 1.165.

17. A gravimetric detector for identifying a 0.5 to 2% buffered hydrogen fluoride (BHF) solution, comprising:

a gravimetric detector comprising a detector column having an inlet end operable to collect a sample of said BHF solution, said detector column formed of an optically transparent material to allow visual observation of said sample in said detector column, and a plurality of specific gravity floats located and moveable within said detector column, wherein one of said plurality of specific gravity floats up at least a portion of a height of said detector column in the presence of said BHF solution and at least one of said plurality of specific gravity floats does not float up in said detector column in said presence of said BHF solution.

18. The detector of claim 17, wherein a specific gravity range of said BHF solution is from 1.100 to 1.165.

19. The detector of claim 17, wherein said optically transparent material comprises silica glass.

* * * * *